(12) United States Patent
Ohkouchi et al.

(10) Patent No.: US 6,740,339 B1
(45) Date of Patent: May 25, 2004

(54) QUICKLY DISINTEGRATING SOLID PREPARATIONS

(75) Inventors: Kazuhiro Ohkouchi, Toyonaka (JP); Hiroyoshi Koyama, Mishima-gun (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/009,835

(22) PCT Filed: Jun. 16, 2000

(86) PCT No.: PCT/JP00/03923

§ 371 (c)(1), (2), (4) Date: Dec. 17, 2001

(87) PCT Pub. No.: WO00/78292

PCT Pub. Date: Dec. 28, 2000

(30) Foreign Application Priority Data

Jun. 18, 1999 (JP) ............................................. 11/172532

(51) Int. Cl.[7] ................................................. A61K 9/20

(52) U.S. Cl. ...................... 424/464; 424/439; 424/440; 424/441; 424/465

(58) Field of Search ................................. 424/464, 465, 424/439, 440, 441

(56) References Cited

FOREIGN PATENT DOCUMENTS

| | | |
|---|---|---|
| EP | 0 839 526 | 5/1998 |
| EP | 0 914 818 | 5/1999 |
| JP | 10-298062 | 11/1998 |
| JP | 2000-119175 | 4/2000 |
| WO | 98/53798 | 12/1998 |
| WO | 00/06126 | 2/2000 |

*Primary Examiner*—James M. Spear
(74) *Attorney, Agent, or Firm*—Wenderoth, Lind & Ponack, L.L.P.

(57) ABSTRACT

Quickly disintegrating solid preparations which contain: a) an active ingredient; b) D-mannitol having an average particle size of 30 μm to 300 μm; c) a disintegrating agent; and d) celluloses.

14 Claims, No Drawings

QUICKLY DISINTEGRATING SOLID PREPARATIONS

TECHNICAL FIELD

The present invention relates to solid preparations that disintegrate quickly in the presence of saliva or a small amount of water in the oral cavity, particularly those useful as intraorally disintegrating solid preparations.

BACKGROUND ART

For aged people and children who are difficult to swallow drugs, solid preparations that disintegrate or dissolve quickly in the oral cavity have long been developed. For example, an intraorally disintegrating tablet preparation is described in the International Publication No. WO93/12769, which is obtained by suspending a drug, lactose, and mannitol in aqueous agar solution, filling the resulting suspension in a molding pocket or the like, and drying the molding under reduced pressure. This molding shows quick disintegration but is more fragile than usual tablets so that it is readily cracked, chipped, etc. and a long time is required for its production; thus the process for production is poor in productivity. In Japanese Patent Laying-Open No.6-218028 (1994) and Japanese Patent Laying-Open No.8-19589 (1996), a process for production of a tablet preparation is described, where moist powder after kneading is filled in the tablet molding well for wet shaping followed by drying. The resulting tablet preparation, being porous and having a moderate void fraction, shows quick disintegration. However the industrial productivity of this process for production is poor because a wet material with low fluidity is filled and compressed so that the amount filled in each well varies greatly and a special dryer is necessary.

Then a few processes for production of an intraorally disintegrating tablet preparation by dry tabletting excellent in productivity have also been reported. For example, a process for production of an intraorally disintegrating tablet preparation by dry tabletting using a saccharide with a good moldability and a saccharide with a poor moldability in combination is described in the International Publication No. WO95/20380. Also a process for production of an intraorally disintegrating tablet preparation by dry tabletting using granules obtained by wet or dry granulation using an excipient and erythritol, a sugar alcohol, in combination is described in the International Publication No. WO98/02185.

In addition, a process for production of a tablet preparation that disintegrates quickly in the oral cavity, by combining a saccharide or a sugar alcohol having a mean particle diameter of not more than 30 μm, an active ingredient, and a disintegrating agent is described in the International Publication No. WO97/47287. According to this process, the molding obtained by pulverization of a saccharide or a sugar alcohol, such as D-mannitol or lactose, followed by addition of a disintegrating agent, etc. and compression molding shows quick disintegration, whereas when coarse particles of a saccharide (lactose, mean particle diameter of 80 μm) or a sugar alcohol (D-mannitol, mean particle diameter of 60 μm) before pulverization are used, molding is difficult under a low tabletting pressure and even the molding obtained under a high tabletting pressure does not show a sufficient mechanical hardness.

D-mannitol is known to produce a very high friction (binding) at the surface of the mortar wall during compression molding. In addition, pulverization is undesirable not only because it strengthens the friction at the surface of the mortar wall but also from the viewpoint of handling because it reduces fluidity during the production of the tablet preparation (Summary of lectures at the $14^{th}$ Symposium on Particulate Preparations and Designs, p.115 (1997), Handbook of Pharmaceutical Excipients $2^{nd}$ Ed., p.294 (1994), The Pharmaceutical Press).

DISCLOSURE OF THE INVENTION

The inventors have conducted extensive studies on intraorally disintegrating tablet preparations that can be industrially produced with common installations without requiring any special manufacturing technique. As the result of the studies, the inventors found that an intraorally disintegrating tablet preparation that has a practically not problematic hardness, disintegrates quickly, and has no problem in productivity can be obtained by dry tabletting even under a low compression pressure when an active ingredient is combined with a relatively coarse powder of a saccharide or a sugar alcohol, a disintegrating agent, and a cellulose compound. As a result of further studies, the inventors have completed the present invention. That is, the invention relates to:

(1) a quickly disintegrating solid preparation comprising a) an active ingredient, b) a saccharide or a sugar alcohol with the mean particle diameter of 30 μm to 300 μm (not less than 30 μm and not more 300 μm), c) a disintegrating agent, and d) a cellulose compound;

(2) the preparation according to the above-mentioned (1), wherein the preparation is an intraorally quickly disintegrating solid preparation;

(3) the preparation according to the above-mentioned (1), wherein the preparation is a tablet preparation;

(4) the preparation according to the above-mentioned (1), wherein 40 to 95 parts of a saccharide or a sugar alcohol is contained in 100 parts of the solid preparation by weight;

(5) the preparation according to the above-mentioned (1), wherein 0.5 to 15 parts of a disintegrating agent is contained in 100 parts of the solid preparation by weight;

(6) the preparation according to the above-mentioned (1), wherein 0.5 to 40 parts of a cellulose compound is contained in 100 parts of the solid preparation by weight;

(7) the preparation according to the above-mentioned (1), wherein the saccharide is one or more saccharides selected from the group consisting of glucose, fructose, lactose, sucrose, and trehalose;

(8) the preparation according to the above-mentioned (1), wherein the saccharide is lactose;

(9) the preparation according to the above-mentioned (1), wherein the sugar alcohol is one or more sugar alcohols selected from the group consisting of D-mannitol, erythritol, xylitol, maltitol, and sorbitol;

(10) the preparation according to the above-mentioned (1), wherein the sugar alcohol is D-mannitol;

(11) the preparation according to the above-mentioned (1), characterized in that D-mannitol with the mean particle diameter of 30 μm to 300 μm is used as the saccharide or sugar alcohol with the mean particle diameter of 30 μm to 300 μm;

(12) the preparation according to the above-mentioned (1), wherein the disintegrating agent is one or more disintegrating agents selected from the group consisting of carmellose calcium, carboxymethylstarch sodium, croscarmellose sodium, and crospovidone;

(13) the preparation according to the above-mentioned (1), wherein the cellulose compound is one or more substances selected from the group consisting of crystalline cellulose, powder cellulose, low substituted hydroxypropylcellulose, and carmellose;

(14) the preparation according to the above-mentioned (1), wherein the active ingredient is manidipine hydrochloride;

(15) the preparation according to the above-mentioned (1), wherein the active ingredient is voglibose;

(16) the preparation according to the above-mentioned (1), wherein the active ingredient is candesartan cilexetil;

(17) the preparation according to the above-mentioned (1), wherein the active ingredient is pioglitazone hydrochloride;

(18) the process for production of the preparation according to the above-mentioned (1), characterized in that a mixture containing a) an active ingredient, b) a saccharide or sugar alcohol with the mean particle diameter of 30 μm to 300 μm (not less than 30 μm and not more than 300 μm), c) a disintegrating agent, and d) a cellulose compound is molded by compression;.

(19) a quickly disintegrating solid preparation containing a) an active ingredient, b-1) a saccharide or sugar alcohol with the mean particle diameter of 5 μm to below 90 μm (not less than 5 μm and below 90 μm), b-2) a saccharide or a sugar alcohol with the mean particle diameter of 90 μm to 500 μm (not less than 90 μm and not more than 500 μm), c) a disintegrating agent, and d) a cellulose compound;

(20) the preparation according to the above-mentioned (19), containing 0.1 to 10 parts of the ingredient b-2) per 1 part of the ingredient b-1) by weight;

(21) the preparation according to the above-mentioned (19), characterized in that a mixture of the ingredient b-1) and the ingredient b-2) as the ingredient b-1) and the ingredient b-2);

(22) the preparation according to the above-mentioned (21), wherein the mean particle diameter of the mixture is 30 μm to 300 μm (not less than 30 μm and not more than 300 μm);

(23) the preparation according to the above-mentioned (19), wherein the mean particle diameter of the ingredient b-1) is 30 μm to below 90 μm (not less than 30 μm and below 90 μm);

(24) the preparation according to the above-mentioned (19), wherein the mean particle diameter of the ingredient b-1) is 35 μm to 80 μm (not less than 35 μm and not more than 80 μm );

(25) the preparation according to (19), wherein the mean particle diameter of the ingredient b-2) is 90 μm to 300 μm (not less than 90 μm and not more than 300 μm );

(26) the preparation according to the above-mentioned (19), wherein the mean particle diameter of the ingredient b-2) is 90 μm to 200 μm (not less than 90 μm and not more than 200 μm );

(27) the preparation according to the above-mentioned (19), wherein the saccharide is one or more saccharides selected from the group consisting of glucose, fructose, lactose, sucrose, and trehalose;

(28) the preparation according to the above-mentioned (19), wherein the saccharide is lactose;

(29) the preparation according to the above-mentioned (19), wherein the sugar alcohol is one or more sugar alcohols selected from the group consisting of D-mannitol, erythritol, xylitol, maltitol, and sorbitol;

(30) the preparation according to the above-mentioned (19), wherein the sugar alcohol is D-mannitol;

(31) the preparation according to the above-mentioned (19), characterized in that D-mannitol with the mean particle diameter of 30 μm to 90 μm and D-mannitol with the mean particle diameter of 90 μm to 300 μm are used as the ingredient b-1) and the ingredient b-2), respectively;

(32) the process for production of a preparation according to the above-mentioned (19), characterized in that a mixture containing a) an active ingredient, b-1) a saccharide or a sugar alcohol with the mean particle diameter of 5 μm to below 90 μm (not less than 5 μm and below 90 μm), b-2) a saccharide or a sugar alcohol with the mean particle diameter of 90 μm to 50 μm (not less than 90 μm and not more than 500 μm), c) a disintegrating agent, and d) a cellulose compound is molded by compression; etc.

Active ingredients used in the present invention may be in any form, i.e. solid, crystal, oil, or solution, and one or more agents selected from the group consisting of, for example, alimentary roborants, antipyretic analgesic antiphlogistics, psychotropic agents, anxiolytics, anti-depressants, hypnotic sedatives, antispasmodics, central nervous system acting drugs, cerebral metabolism improving agents, cerebral circulation improving agents, antiepileptics, sympathomimetics, digestives, antacids, antiulcer agents, antitussive expectorants, antiemetics, respiratory stimulants, bronchodilators, antiallergic agents, dental stomatic agents, anti-histamines, cardiacs, antiarrhythmic agents, diuretics, hypotensive agents, angiotonics, coronary vasodilators, peripheral vasodilators, antihyperlipemic drugs, cholagogues, antibiotics, chemotherapeutics, antidiabetic agents, osteoporosis treating drugs, antirheumatics, skeletal muscle relaxants, antispasmodic drugs, hormone drugs, alkaloid narcotics, sulfa drugs, gout treating agents, anticoagulants, antineoplastic agents, and the like are used.

Alimentary roborants include vitamins such as vitamin A, vitamin D, vitamin E (d-α-tocopherol acetate, etc.), vitamin B1 (dibenzoyl thiamine, fursultiamine hydrochloride, etc.), vitamin B2 (riboflavin butyrate, etc.), vitamin B6 (pyridoxine hydrochloride, etc.), vitamin C (ascorbic acid, sodium L-ascorbate, etc.), and vitamin B12 (hydroxocobalamin acetate, cyanocobalamin, etc.), minerals such as calcium, magnesium, iron, etc., protein, amino acids, oligosaccharides, crude drugs, and the like.

Antipyretic analgesic antiphlogistics include aspirin, acetaminophen, ethenzamide, ibuprofen, diphenhydramine hydrochloride, chlorpheniramine dl-maleate, dihydrocodeine phosphate, noscapine, methylephedrine hydrochloride, phenylpropanolamine hydrochloride, caffeine, anhydrous caffeine, serrapeptase, lysozyme chloride, tolfenamic acid, mefenamic acid, diclofenac sodium, flufenamic acid, salicylamide, aminopyrine, ketoprofen, indometacin, bucolome, pentazocine, and the like.

Psychotropic agents include chlorpromazine, reserpine, and the like. Anxiolytics include alprazolam, chlordiazepoxide, diazepam, and the like. Antidepressants include imipramine, maprotilline hydrochloride, amphetamine, and the like. Hypnotic sedatives include estazolam, nitrazepam, diazepam, perlapine, phenobarbital sodium, and the like. Antispasmodics include scopolamine hydrobromide, diphenhydramine hydrochloride, papaverine hydrochloride, and the like. Central nervous system acting agents include citicoline, and the like. Cerebral metabolism improving agents include meclofenoxate hydrochloride, and the like. Cerebral circulation improving agents include vinpocetine, and the like. Antiepileptics include phenytoin, carbamazepine, and the like. Sympathomimetics include isopreterenol hydrochloride, and the like.

Digestives include stomachic digestives such as diastase, saccharated pepsin, scopolia extract, cellulase AP3, lipase AP, cinnamon oil, etc., and drugs for controlling intestinal function such as berberine chloride, antibiotics-resistant lactic acid bacteriae, lactobacillus bifidus, etc. Antacids include magnesium carbonate, sodium bicarbonate, magnesium aluminometasillicate, synthetic hydrotalcite, precipitated calcium carbonate, magnesium oxide, and the like. Anti-ulcer agents include lansoprazole, omeprazol, rabeprazole, famotidine, cimetidine, ranitidine hydrochloride, and the like.

Antitussive expectorants include chloperastine hydrochloride, dextromethorphane hydrobromide, theophylline, potassium guaiacolsulfonate, guaifenesin, codeine phosphate, and the like. Antiemetics include difenidol hydrochloride, metoclopramide, and the like. Respiratory stimulants include levallorphan tartrate, and the like. Bronchodilators include theophylline, salbutamol sulfate, and the like. Antiallergic agents include amlexanox, seratrodast, and the like.

Dental stomatic agents include oxytetracycline, triamcinolone acetonide, chlorhexidine hydrochloride, lidocaine, and the like.

Antihistamines include diphenhydramine hydrochloride, promethazine, isothipendyl hydrochloride, chlorpheniramine dl-maleate, and the like.

Cardiacs include caffeine, digoxin, and the like. Antiarrhythmic agents include procainamide hydrochloride, propranolol hydrochloride, pindolol, and the like. Diuretics include isosorbide, furosemide, hydrochlorothiazide, and the like. Hypotensive agents include derapril hdyrochloride, captopril, hydraladine hydrochloride, labetalol hydrochloride, manidipine hydrochlorodie, candesartan cilexetil, methyldopa, perindopril erbumine, and the like. Angiotonics include phenylepherine hydrochloride, and the like. Coronary vasodilators include carbocromen hydrochloride, molsidomine, verapamil hydrochloride, and the like. Peripheral vasodilators include cinnarizine, and the like.

Antihyperlipemic agents include cerivastatin sodium, simvastain, pravastatin sodium, atorvastatin calcium hydrate, and the like.

Cholagogues include dehydrocholic acid, trepibutone, and the like.

Antibiotics include cefems such as cefalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, etc., synthetic ones such as ampicillin, ciclacillin, nalidixic acid, enoxacin, etc., monobactams such as carumonam sodium, penems, carbapenems, and the like.

Chemotherapeutics include sulfamethizole, and the like.

Antidiabetic agents include tolbutamide, voglibose, pioglitazone hydrochloride, glibenclamide, troglitazone, and the like.

Osteoporosis treating drugs include ipriflavone, and: the like.

Skeletal muscle relaxants include methocarbamol, and the like.

Antispasmodic drugs meclizine hydrochloride, dimenhydrinate, and the like.

Antirheumatics include methotrexate, bucillamine, and the like.

Hormone drugs include liothyronine sodium, dexamethasone phosphate, predonisolone, oxendolone, leuprorelin acetate, and the like.

Alkaloid narcotics include opium, morphine hydrochloride, ipecac, oxycodone hydrochloride, opium alkaloids hydrochloride, cocaine hydrochloride, and the like.

Sulfa drugs include sulfisomidine, sulfamethizole, and the like.

Gout treating drugs include allopurinol, colchicine, and the like.

Anticoagulants include dicoumarol, and the like.

Antineoplastic drugs include 5-fluorouracil, uracil, mitomycin, and the like.

Among these, manidipine hydrochloride,voglibose, candesartan cilexetil, pioglitazone hydrochloride, etc., particularly manidipine hydrochloride, are used preferably.

The active ingredient may be the one diluted with a diluent used generally in the fields of medicine and foods. An active ingredient after treatment for masking the bitterness of the active ingredient may also be used.

The amount of the active ingredient varies depending on the nature and dose of the active ingredient, and is 0.01 to 40 parts, preferably 0.01 to 20 parts, per 100 parts by weight of the solid pharmaceutical preparation of the invention.

Saccharides used in the invention include glucose, fructose, lactose, sucrose, trehalose, and the like, among which lactose is used preferably.

Sugar alcohols used in the invention include D-mannitol, erythritol, xylitol, maltitol, sorbitol, and the like, among which D-mannitol is used preferably.

One or more saccharides or one or more sugar alcohols may be used in combination, or a combination of a saccharide and a sugar alcohol may be used.

The mean particle diameter of the saccharide or the sugar alcohol (preferably the sugar alcohol, or more preferably D-mannitol) is 30 to 300 $\mu$m (measured by, for example, the laser diffraction particle size analyzer, SYMPATEC Co.: HELOS & RODOS, etc.), preferably above 30 $\mu$m, more preferably 31 $\mu$m or more, and further more preferably 35 to 200 $\mu$m. Saccharides or sugar alcohols of such a particle size are commercially available (Lactose 100M and Lactose 200M of DMV, granulated powder lactose Dilactose R and Dilactose S of Freund Industry Co., Ltd., Tablettose and Flowlac 100 of Meggle Japan, Mannit S and Marinecrystal of Towa Chemical Industry Co., Ltd., 1.05980 of Merck Co., Mannidex of Cerestar Japan, Ltd., Trehalose P of Asahi Chemical Industry Co., Ltd., Sorbitol DP-50M and Amalty MR-50 of Towa Chemical Industry Co., Ltd., Pure Fructose S of Kato Kagaku, and the like). Saccharides and sugar alcohols with the mean particle diameter of 5 to 30 $\mu$m are commercially available (Granulac 230 and Solvolac 400 of Meggle Japan, Mannit P, Xylit P, and Amalty MR-100 of Towa Chemical Industry Co., Ltd., Erythritol (fine powder) of Nikken Chemicals Co., Ltd., and the like). Saccharides and sugar alcholos with the mean particle diameter of 200 to 500 $\mu$m are commercially available (Sachelac 80 of Meggle Japan, Trehalose G and Xylitol XC of Asahi Chemical Industry Co., Ltd., Erythritol of Nikken Chemicals Co., Ltd., Anhydrous crystalline glucose TDA-S and Hydrated crystalline glucose TDH of San-ei Sucrochemical Co., Ltd., and the like). In addition, saccharides and sugar alcohols with the mean particle diameter of not less than 500 $\mu$m are commercially available (Prismalac 40 of Meggle Japan, Pure Fructose of Kato Kagaku, Amalty MR-20 and Sorbitol DP-10M of Towa Chemical Industry Co., Ltd., and the like).

A saccharide or sugar alcohol with the necessary mean particle diameter may be obtained by a method such as pulverization from the commercially available product. Pulverization is performed by using a cutter mill, jet mill, hammer mill, or the like.

A saccharide or sugar alcohol with the mean particle diameter of 5 μm to below 90 μm (preferably 30 to below 90 μm) to strengthen the molding may be combined with a saccharide or sugar alcohol with the mean particle diameter of 90 μm to 500 μm (preferably 90 μm to 300 μm) to increase fluidity during manufacturing. In combination of a fine powder of a saccharide or sugar alcohol with the mean particle diameter of 5 μm to below 90 μm (preferably 30 to below 90 μm, more preferably 35 to 80 μm) with a coarse powder of a saccharide or sugar alcohol with the mean particle diameter of 90 μm to 500 μm (preferably 90 μm to 300 μm, more preferably 90 to 200 μm), it is recommendable to use one part of a fine powder of a saccharide or sugar alcohol with 0.1 to 10 parts, preferably 0.2 to 5 parts, of a coarse powder of a saccharide or sugar alcohol by weight. Particularly when the active ingredient is manidipine hydrochloride, it is recommendable to use one part of a fine powder of a saccharide or sugar alcohol usually with 0.2 to 3.5 parts, preferably with 0.3 to 2.5 parts, of a coarse powder of a saccharide or sugar alcohol by weight.

In combination of a fine powder of a saccharide or sugar alcohol with a coarse powder of a saccharide or sugar alcohol, one or more saccharides or one or more sugar alcohols may be combined, or a fine powder of a saccharide or sugar alcohol may be combined with a coarse powder of the same or a different saccharide or sugar alcohol. In addition, a mixture obtained by mixing a fine powder of a saccharide or sugar alcohol with a coarse powder of a saccharide or sugar alcohol may be molded into a quickly disintegrating solid preparation of the invention, or a fine powder of a saccharide or sugar alcohol and a coarse powder of a saccharide or sugar alcohol are divided into two or more groups to prepare granules, followed by molding into the quickly disintegrating solid preparation of the invention.

When the mixture of a fine powder of a saccharide or sugar alcohol with a coarse powder of a saccharide or sugar alcohol is used as the starting material, the mixture has desirably two or more peaks in the particle size distribution and the mean particle diameter of the mixture is desirably 30 μm to 300 μm.

A desirable combination of a fine powder of a saccharide or sugar alcohol with a coarse powder of a saccharide or sugar alcohol is exemplified by the mixture of D-mannitol with the mean particle diameter of 30 μm to below 90 μm with D-mannitol with the mean particle diameter of 90 μm to 300 μm.

The amount of a saccharide or sugar alcohol used is 40 to 95 parts, preferably 50 to 90 parts, per 100 parts of the solid pharmaceutical preparation by weight.

Disintegrating agents used include carmellose calcium, carboxymethyl starch sodium, croscarmellose sodium, crospovidone, and the like, and 0.5 to 15 parts, preferably 1 to 10 parts, thereof is used per 100 parts of the solid pharmaceutical preparation by weight.

Disintegrating agents are exemplified by Crospovidone [manufactured by ISP Inc. (USA), BASF (Germany)], Croscarmellose Sodium (FMC-Asahi Chemical Industry Co., Ltd.), Carmellose Calcium (Gotoku Yakuhin Co., Ltd.), and Carboxymethylstarch Sodium (Matsutani Kagaku Co., Ltd., Kimura Sangyo Co., Ltd., etc.).

The crospovidone product may be any cross-linked polymer that is 1-ethenyl-2-pyrrolidinone homopolymer, and usually a crospovidone product having a molecular weight of 1,000,000 or more is used. Examples of commercially available crospovidone products are Cross-linked Povidone, Kollidon CL [manufactured by BASF (Germany)], Polyplasdone XL, Xl-10, and INF-10 [manufactured by ISP Inc. (USA)].

Cellulose compounds used are crystalline cellulose, powder cellulose, low substituted hydroxypropylcellulose, carmellose, and the like, and 0.5 to 40 parts, preferably 1 to 20 parts, thereof is used for 100 parts of the solid pharmaceutical preparation by weight.

Examples of crystalline cellulose products are CEOLUS KG801, Avicel PH101, PH102, PH301, PH302, and PH-F20, Avicel RC-A591NF (all manufactured by Asahi Chemical Industry Co., Ltd.), and the like, including also fine crystalline cellulose.

Examples of low substituted hydroxypropylcellulose products are low substituted hydroxylpropylcellulose of which content of hydroxypropoxyl group is 5 to 16% by weight such as Low Substituted Hydroxypropylcellulose LH11, LH21, LH31, LH22, LH32, LH20, LH30, LH32, and LH33 (all manufactured by Shin-Etsu Chemical Co., Ltd.), and the like. These are commercially available. Low substituted hydroxypropylcellulose can be produced by a publicly known procedure, for example the procedure described in Patent Gazette No.57-53100(1982), or a similar procedure.

Active ingredients, disintegrating agents, and cellulose compounds may be used in combination of one or more of each.

The preparation of the invention may contain a starch product as an excipient such as corn starch, potato starch, wheat starch, rice starch, partially gelatinized starch, gelatinized starch, porous starch, and the like, and various additives used for production of general pharmaceutical preparations, in their respective suitable amounts, unless they interfere with the effect of the invention. Such additives include excipients, binders, sour agents, foaming agents, artificial sweeteners, flavoring agents, lubricants, colorants, stabilizers, pH-modifiers, surfactants, and the like.

Excipients include inorganic excipients such as anhydrous calcium phosphate, precipitated calcium carbonate, calcium silicate, light anhydrous silicic acid, and the like.

Binders include hydroxypropylcellulose, hydroxypropylmethylcellulose, polyvinylpyrrolidone, powdered acacia, gelatin, pullulan, and the like.

Sour agents include citric acid, tartaric acid, malic acid, ascorbic acid, and the like.

Foaming agents include sodium bicarbonate, sodium carbonate, and the like. Sweeteners include saccharin sodium, dipotassium glycylrrhizinate, aspartame, stevia, thaumatin, and the like.

Flavoring agents include lemon oil, orange oil, menthol, and the like.

Lubricants include magnesium stearate, sucrose esters of fatty acid, polyethyleneglycol, talc, stearic acid, sodium stearylfumarate, and the like.

Colorants include those for food such as Food Yellow No.5, Food Red No.2, Food Blue No.2, and the like, food lake colorants, ferric oxide, and the like.

Stabilizers include disodium edetate, tocopherol, cyclodextrin, and the like.

pH-Modifiers include citrates, phosphates, carbonates, tartarates, fumarates, acetates, amino acid salts.

Surfactants include sodium lauryl sulfate, polysorbate 80, hydrogenated oil, polyoxyethylene(160)polyoxypropylene (30)glycol, and the like.

The particle diameter of these substances is not particularly limited, but the particle diameter is preferably not more than 500 μm not to cause rough feeling in the mouth. These excipients may be used separately or in combination of two or more thereof.

A fine granular nucleus may be used for manufacturing of the solid preparation of the invention, and such a nucleus may be coated with active ingredients and additives etc. followed by further coating by a publicly known procedure for masking of the taste/odor, for enteric coating, for making the preparation into a sustained release form, and for other purposes.

The solid preparation of the invention can be produced either by compression molding of a mixture comprising a) an active ingredient, b) a saccharide or sugar alcohol with the mean particle diameter of 30 μm to 300 μm, c) a disintegrating agent, and d) a cellulose compound, or by compression molding of a mixture comprising a) an active ingredient, b-1) a saccharide or sugar alcohol with the mean particle diameter of 5 μm to below 90 μm, b-2) a saccharide or sugar alcohol with the mean particle diameter of 90 μm to 500 μm, c) a disintegrating agent, and d) a cellulose compound.

The procedures for production by dividing the starting materials into two groups are exemplified by:

[1] compression molding by mixing a group comprising a) an active ingredient, b-1) a saccharide or sugar alcohol with the mean particle diameter of 5 μm to below 90 μm, c) a disintegrating agent, and d) a cellulose compound, and a group comprising b-2) a saccharide or sugar alcohol with the mean particle diameter of 90 μm to 500 μm, c) a disintegrating agent, and d) a cellulose compound, followed by addition of a fluidizing agent, lubricant, sweetener, and/or the like in their respective suitable amounts, as needed;

[2] compression molding by mixing a group comprising a) an active ingredient, b-1) a saccharide or sugar alcohol with the mean particle diameter of 5 μm to below 90 μm, and c) a disintegrating agent, and a group comprising b-2) a saccharide or sugar alcohol with the mean particle diameter of 90 μm to 500 μm, c) a disintegrating agent, and d) a cellulose compound, followed by addition of a cellulose compound, fluidizing agent, lubricant, sweetener, and/or the like in their respective suitable amounts as needed;

[3] compression molding by mixing a group comprising a) an active ingredient, b-1) a saccharide or sugar alcohol with the mean particle diameter of 5 μm to below 90 μm, b-2) a saccharide or sugar alcohol with the mean particle diameter of 90 μm to 500 μm, c) a disintegrating agent, and d) a cellulose compound as needed, and a group comprising b-1) a saccharide or sugar alcohol with the mean particle diameter of 5 μm to below 90 μm, b-2) a saccharide or sugar alcohol with the mean particle diameter of 90 μm to 500 μm, c) a disintegrating agent, and d) a cellulose compound, followed by addition of a cellulose compound, fluidizing agent, lubricant, sweetener, and/or the like in their respective suitable amounts as needed.

The concrete procedures for production include the procedure that an active ingredient and the raw materials of the preparation are mixed in a mixer followed by immediate tabletting. Also the procedure that the materials are dry compressed into tablets by the slugging method or roller-compacter method, the procedure for production of granules for tablets by dry tabletting using water, acetone, ethyl alcohol, propyl alcohol, or a mixture thereof, in which a binder, if necessary, has been dispersed or dissolved, and the procedure for production of granules for tablets after dividing the materials into two or more groups may be applicable. For production of tablets from granules for tablets, a cellulose compound, a disintegrating agent, a fluidizing agent, a lubricant, a flavoring agent, a sweetener, and the like may be mixed as needed.

Tablets are molded by using, for example, a single tabletting machine, rotary tabletting machine, and the like. Pressure for tabletting is usually 2.5 to 30 kN/cm$^2$. The shape of the solid preparation of the invention is not particularly restricted; the tablet may be round, caplet, doughnut, oblong, etc. or a multilayer tablet, a dry-coated tablet, or the like, and may be covered by coating. The tablet may have marks and letters for identification, and a nick on the surface.

The resultant quickly disintegrating solid preparation, preferably intraorally quickly disintegrating solid preparation, more preferably, intraorally quickly disintegrating tablet of the invention is quickly disintegrated in the oral cavity and has an adequate hardness. It is excellent also in productivity.

Namely, the time required for intraoral disintegration or dissolution (the time till the tablet is completely disintegrated by the action of the saliva in the oral cavity of healthy adult men and women) of the intraorally quickly disintegrating tablet of the invention varies depending to the size and thickness of the tablet, being normally 5 to 90 seconds, preferably about 5 to 60 seconds. The hardness (measured by the tablet hardness meter) is normally 10 to 200N, preferably about 10 to 150 N.

Therefore the intraorally disintegrating tablet of the invention, like the conventional pharmaceutical preparations containing active ingredients, can be used for treatment and prevention of various diseases as a tablet easy to be taken by patients, aged people, and children who are difficult to swallow the medicine, and as a safe preparation in emergency for general adult people, and is excellent in long-term storage and stability.

The preparation may be orally taken without being disintegrated in the oral cavity, or taken with water. The preparation may also be orally taken after being dissolved in water in a cup or the like.

THE BEST MODE FOR CARRYING OUT THE INVENTION

The invention is explained in more detail with the following Examples and Comparative Examples, though these Examples do not limit the invention.

EXAMPLES

The tablet preparations obtained in the Examples and in the Comparative Examples were subjected to the test methods described below for measurement of the hardness and the intraoral disintegration time. Also productivity was assessed based on the observation of fluidity, binding property, and adhesion of powder to the surface of the punch during production of the tablet.

(1) Hardness Test

Hardness was measured with the tablet hardness meter (Toyama Sangyo Co., Ltd.). Hardness of each of 5 or 10 tablets was measured, and expressed in the mean of the measurements.

(2) Intraoral Disintegration Time

The time till disintegration of the tablet in the presence of saliva alone in the oral cavity was measured in 3 healthy adult men (35, 49, and 51 years old).

Example 1

A 40 g portion of manidipine hydrochloride, 303.4 g of D-mannitol (Towa Chemical Industry Co., Ltd.: Mannit S, mean particle diameter of 130 μm), 50 g of crystalline cellulose (Asahi Chemical Industry Co., Ltd.), 50 g of corn starch (Japan Corn Starch), and 1 g of light anhydrous silicic acid (YKF) were placed in a fluidized bed granulating dryer (Powrex Co., LAB-1 type), and 139 g of purified water containing 18 g of D-mannitol and 0.6 g of yellow ferric oxide (Anstead) was sprayed, followed by granulating and drying processes, to give granules.

To 347 g of the granules, 25 g of crospovidone (ISP Inc.), 1 g of light anhydrous silicic acid, 10 g of magnesium stearate (Taihei Kagaku Sangyo Co. Ltd.), and 1 g of aspartame (Ajinomoto Co. Ltd.) were added, to give a mixed powder.

This mixed powder was tabletted into tablets weighing 250 mg each (Kikusui Seisakusho, Correct 12HUK, tablet size of 9.5 mmφ, compression pressure of 9.8 kN (1 ton)/cm$^2$).

Example 2

A 180 g portion of manidipine hydrochloride, 495 g of D-mannitol (Merck Co.: 1.05980, mean particle diameter of 45 μm), 225 g of corn starch, 112.5 g of crystalline cellulose, 2 g of light anhydrous silicic acid, and 56.3 g of crospovidone were placed in a fluidized bed granulating dryer (Powrex Co., FD-3SN type), and 540 g of purified water containing 42.8 g of D-mannitol and 1.4 g of yellow ferric oxide was sprayed, followed by granulating and drying processes, to give granules A.

Separately, 872.1 g of D-mannitol (Towa Chemical Industry Co., Ltd.: Mannit S), 112.5 g of crystalline cellulose, and 56.3 g of crospovidone were placed in a fluidized bed granulating dryer (Powrex Co., FD-3SN type), and 540 g of purified water containing 36.2 g of D-mannitol and 1.4 g of yellow ferric oxide was sprayed, followed by granulating and drying processes, to give granules B.

A 1003 g portion of granules A, 971 g of granules B, 6.3 g of light anhydrous silicic acid, 4.1 g of aspartame, and 41 g of magnesium stearate were mixed.

This mixed powder was tabletted into tablets weighing 250 mg each (Kikusui Seisakusho, Correct 12HUK, tablet size of 9.5 mmφ, compression pressure of 4.9, 9.8, and 19.6 kN /cm$^2$).

Example 3

A 90 g portion of manidipine hydrochloride, 416 g of D-mannitol (Merck Co.: 1.05980, mean particle diameter of 45 μm), 189 g of corn starch, 94.5 g of crystalline cellulose, 1.7 g of light anhydrous silicic acid, and 47.3 g of crospovidone were placed in a fluidized bed granulating dryer (Powrex Co., FD-3SN type), and 423 g of purified water containing 33.5 g of D-mannitol and 0.4 g of yellow ferric oxide was sprayed, followed by granulating and drying processes, to give granules C.

Separately, 884 g of D-mannitol (Towa Chemical Industry Co., Ltd.: Mannit S), 105 g of crystalline cellulose, and 52.5 g of crospovidone were placed in a fluidized bed granulating dryer (Powrex Co., FD-3SN type), and 540 g of purified water containing 35.7 g of D-mannitol and 0.4 g of yellow ferric oxide was sprayed, followed by granulating and drying processes, to give granules D.

A 760 g portion of granules C, 845 g of granules D, 5.1 g of light anhydrous silicic acid, 3.9 g of aspartame, and 33 g of magnesium stearate were mixed.

This mixed powder was tabletted into tablets weighing 210 mg each (Kikusui Seisakusho, Correct 12HUK, tablet size of 9.0 mmφ, compression pressure of 9.8 kN/cm$^2$).

Example 4

An 80 g portion of manidipine hydrochloride, 220 g of D-mannitol (Merck Co.: 1.05980, mean particle diameter of 45 μm), 100 g of corn starch, and 1.2 g of light anhydrous silicic acid were placed in a fluidized bed granulating dryer (Powrex Co., LAB-1 type), and 200 g of purified water containing 6 g of hydroxypropylcellulose (Nippon Soda Co., Ltd.) and 0.4 g of yellow ferric oxide was sprayed, followed by granulating and drying processes, to give granules E.

Separately, 400.5 g of D-mannitol (Towa Chemical Industry Co., Ltd.: Mannit S), and 100 g of crystalline cellulose were placed in a fluidized bed granulating dryer (Powrex Co., LAB-1 type), and 180 g of purified water containing 16.1 g of D-mannitol and 0.8 g of yellow ferric oxide was sprayed, followed by granulating and drying processes, to give granules F.

A 203.8 g portion of granules E, 258.8 g of granules F, 25 g of crospovidone, 1.4 g of light anhydrous silicic acid, 1 g of aspartame, and 10 g of magnesium stearate were mixed.

This mixed powder was tabletted into tablets weighing 250 mg each (Kikusui Seisakusho, Correct 12HUK, tablet size of 9.5 mmφ, compression pressure of 9.8 kN/cm$^2$).

Example 5

A 289 g portion of D-mannitol (Towa Chemical Industry Co., Ltd.: Mannit S), 40 g of crystalline cellulose, 40 g of corn starch, and 1.2 g of light anhydrous silicic acid were placed in a fluidized bed granulating dryer (Powrex Co., LAB-1 type), and 120 g of purified water containing 0.4 g of voglibose and 10 mg of Food Yellow No.5 was sprayed, followed by granulating and drying processes, to give granules.

To 296 g of the granules, 16 g of crospovidone, 0.32 g of light anhydrous silicic acid, 6.4 g of magnesium stearate, and 0.96 g of aspartame were added, to give a mixed powder.

This mixed powder was tabletted into tablets weighing 200 mg each (Kikusui Seisakusho, Correct 12HUK, tablet size of 9.0 mmφ, compression pressure of 9.8 kN/cm$^2$).

Example 6

A 16 g portion of candesartan cilexetil, 273 g of D-mannitol (Towa Chemical Industry Co., Ltd.: Mannit S):, 40 g of crystalline cellulose, 40 g of corn starch, and 1.2 g of light anhydrous silicic acid were placed in a fluidized bed granulating dryer (Powrex Co., LAB-1 type), and 120 g of purified water was sprayed, followed by granulating and drying processes, to give granules.

To 296 g of the granules, 16 g of crospovidone, 0.32 g of light anhydrous silicic acid, 6.4 g of magnesium stearate, and 0.96 g of aspartame were added, to give a mixed powder.

This mixed powder was tabletted into tablets weighing 200 mg each (Kikusui Seisakusho, Correct 12HUK, tablet size of 9.0 mmφ, compression pressure of 9.8 kN/cm$^2$).

Example 7

A 660 mg portion of pioglitazone hydrochloride, 2670 mg of D-mannitol (Towa Chemical Industry Co., Ltd.: Mannit S), 500 mg of crystalline cellulose, 500 mg of corn starch, 500 mg of crospovidone, 20 mg of light anhydrous silicic acid, 100 mg of magnesium stearate, and 50 mg of aspartame were mixed in a tablet bottle.

This mixed powder was tabletted into tablets weighing 250 mg each (Shimadzu Corporation, Universal testing machine UH-10A, tablet size of 9.5 mmφ, compression pressure of 9.8 kN/cm$^2$).

Example 8

A 900 g portion of manidipine hydrochloride, 1374.8 g of granulated lactose powder (Freund Sangyo.: Dilactose S, mean particle diameter of 80 μm), 301.5 g of crospovidone, and 211.5 g of corn starch (Japan Corn Starch) were placed in a fluidized bed granulating dryer (Fuji Sangyo Co., Ltd., FD-5S type), and 4500 g of purified water containing 225 g of hydroxypropylcellulose (Nippon Soda Co., Ltd.) and 2.3 g of yellow ferric oxide was sprayed, followed by granulating and drying processes, to give granules G. The granules G were sized at the screen size (1.0 mmφ) by a power mill (Showa Kagaku Kikai Kosakusho, P-3), to give sized granules G.

Separately, 2856 g of D-mannitol (Towa Chemical Industry Co., Ltd.: Mannit S), 1650 g of D-mannitol (Merck Co.: 1.05980), and 249 g of crospovidone were placed in a fluidized bed granulating dryer (Fuji Sangyo Co., Ltd., FD-5S type), and 1500 g of purified water containing 150 g of D-mannitol (Towa Chemical Industry Co., Ltd.: Mannit S), 7.5 g of yellow ferric oxide, and 37.5 g of anhydrous citric acid was sprayed, followed by granulating and drying processes, to give granules H. The granules G were sized at the screen size (1.0 mm) by a power mill, to give sized granules H.

A 737 g portion of sized granules G, 1815 g of sized granules H, 151.3 g of crystalline cellulose, 5.5 g of aspartame, and 41.3 g of magnesium stearate were mixed. This mixed powder was tabletted into tablets weighing 250 mg each (Kikusui Seisakusho, Correct 12HUK, tablet size of 9.5 mmφ, compression pressure of 7.4 kN /cm$^2$).

Example 9

A 44 g portion of manidipine hydrochloride, 442.4 g of trehalose (Asahi Chemical Industry Co., Ltd.: Trehalose P, mean particle diameter of 44 μm), and 33 g of crospovidone were placed in a fluidized bed granulating dryer (Powrex Co., LAB-1 type), and 231 g of purified water containing 11 g of hydroxypropylcellulose was sprayed, followed by granulating and drying processes, to give granules.

A 459.4 g portion of the granules, 27.2 g of crystalline cellulose, 1.0 g of aspartame, and 7.4 g of magnesium stearate were mixed.

This mixed powder was tabletted into tablets weighing 250 mg each (Kikusui Seisakusho, Correct 19KAWC, tablet size of 9.5 mmφ, compression pressure of 2.9 kN/cm$^2$).

Example 10

Trehalose (Asahi Chemical Industry Co., Ltd.: Trehalose G, mean particle diameter of 346 μm) was pulverized with a power mill (Showa Kagaku Kikai Kosakusho, P-3) at the screen size (0.5 mmφ), to give a powder with the mean particle diameter of 185 μm.

This pulverized trehalose was used in place of the trehalose in Example 9, and processed under the same conditions as those in Example 9, to give tablets.

Example 11

Erythritol (Nikkenn Chemicals Co., Ltd.: mean particle diameter of 474 μm) was pulverized with a power mill (Showa Kagaku Kikai Kosakusho, P-3) at the screen size (0.5 mmφ), to give a powder with the mean particle diameter of 178 μm.

This pulverized erythritol was used in place of the trehalose in Example 9, and processed under the same conditions as those in Example 9, to give tablets. (compression pressure 7.4 kN/cm$^2$).

Example 12

Xylitol (Towa Chemical Industry Co., Ltd.: Xylit XC, mean particle diameter of 363 μm) was pulverized with a power mill (Showa Kagaku Kikai Kosakusho, P-3) at the screen size (0.5 mmφ), to give a powder with the mean particle diameter of 135 μm.

A 50 g portion of manidipine hydrochloride, the pulverized xylitol, 37.5 g of crospovidone, 15.6 g of crystalline cellulose, and 9.4 g of magnesium stearate were mixed.

This mixed powder was tabletted into tablets weighing 250 mg each (Shimadzu Corporation, Universal testing machine UH-10A, tablet size of 9.5 mmφ, compression pressure of 14.7 kN /cm$^2$).

Example 13

A 50 g portion of manidipine hydrochloride, maltitol (LESYS of Towa Chemical Industry Co., Ltd., mean particle diameter of 181 μm), 37.5 g of crospovidone, 15.6 g of crystalline cellulose, and 9.4 g of magnesium stearate were mixed.

This mixed powder was tabletted into tablets weighing 250 mg each (Shimadzu Corporation, Universal testing machine UH-10A, tablet size of 9.5 mmφ, compression pressure of 9.8 kN /cm$^2$).

Example 14

Erythritol (Nikkenn Chemicals Co., Ltd.: mean particle diameter of 474 μm) was pulverized with a jet mill (Nippon Pneumatic MFG Co., Ltd., PJM-100SP), to give a powder with the mean particle diameter of 75 μm.

This pulverized erythritol was used in place of the trehalose in Example 9, and processed under the same conditions as those in Example 9, to give tablets.

Example 15

Sorbitol (Sorbitol DP-50M of Towa Chemical Industry Co., Ltd., mean particle diameter of 172 μm) was pulverized with a jet mill (Nippon Pneumatic MFG Co., Ltd., PJM-100SP), to give a powder with the mean particle diameter of 43 μm.

A 25 g portion of manidipine hydrochloride, the pulverized sorbitol, 18.8 g of crospovidone, 7.8 g of crystalline cellulose, and 4.7 g of magnesium stearate were mixed.

This mixed powder was tabletted into tablets weighing 125 mg each (Shimadzu Corporation, Universal testing machine UH-10A, tablet size of 8.5 mmφ, compression pressure of 2.9 kN /cm$^2$).

Comparative Example 1

D-Mannitol with the mean particle diameter of 21 μm (Merck Co., 1.05988) was used in place of the D-mannitol in Example 1, and processed under the same conditions as those in Example 1, to give tablets.

Comparative Example 2

D-Mannitol with the mean particle diameter of 21 μm (Merck Co.: 1.05988) was used in place of the D-mannitol in Example 5, and processed under the same conditions as those in Example 5, to give tablets.

Comparative Example 3

Trehalose (Asahi Chemical Industry Co., Ltd.: Trehalose G) was pulverized with the atomizer (Fuji Paudal Co., Ltd., KII-2), to give a powder with the mean particle diameter of 19 μm.

This pulverized trehalose was used in place of the trehalose in Example 9, and processed under the same conditions as those in Example 9, to give tablets.

The results of measurement of the hardness and the intraoral disintegration time of the tablets obtained in the Examples and Comparative Examples by the above-mentioned test methods, and the results of evaluation of productivity based on the observation of fluidity, binding property, and adhesion of powder to the surface of the punch during production of tablets are summarized in Table 1.

TABLE 1

Productivity, hardness, and intraoral disintegration time of tablets

|  | Tabletting pressure (kN/cm$^2$) | Fluidity during tabletting | Binding property | Adhesion to punch | Hardness (N) | Intraoral disintegration time (second) |
| --- | --- | --- | --- | --- | --- | --- |
| Example 1 | 9.8 | good | absent | absent | 37 | 25 |
| Example 2 | 4.9 | good | absent | absent | 17 | 17 |
|  | 9.8 | good | absent | absent | 39 | 16 |
|  | 19.6 | good | absent | absent | 50 | 20 |
| Example 3 | 9.8 | good | absent | absent | 24 | 17 |
| Example 4 | 9.8 | good | absent | absent | 25 | 24 |
| Example 5 | 9.8 | good | absent | absent | 26 | 19 |
| Example 6 | 9.8 | good | absent | absent | 26 | 13 |
| Example 7 | 9.8 | good | absent | absent | 33 | 25 |
| Example 8 | 7.4 | good | absent | absent | 29 | 22 |
| Example 9 | 2.9 | good | absent | absent | 21 | 52 |
| Example 10 | 2.9 | good | absent | absent | 16 | 43 |
| Example 11 | 7.4 | good | absent | absent | 36 | 31 |
| Example 12 | 14.7 | good | absent | absent | 16 | 61 |
| Example 13 | 9.8 | good | absent | absent | 21 | 51 |
| Example 14 | 2.9 | good | absent | absent | 17 | 38 |
| Example 15 | 2.9 | good | absent | absent | 16 | 67 |
| Comparative Example 1 | 9.8 | insufficient | present | present | 49 | 26 |
| Comparative Example 2 | 9.8 | insufficient | present | present | 33 | 21 |
| Comparative Example 3 | 2.9 | insufficient | present | present | 25 | 36 |

INDUSTRIAL APPLICABILITY

Quickly disintegrating solid preparations, preferably intraorally quickly disintegrating solid preparations, more preferably intraorally quickly disintegrating tablets of the invention obtained by the processes described above are quickly disintegrated in the oral cavity and have suitable hardness. They are excellent also in productivity.

What is claimed is:

1. A quickly disintegrating solid preparation comprising a) an active ingredient, b-1) a saccharide or sugar alcohol with a mean particle diameter of 5 μm to below 90 μm, b-2) a saccharide or sugar alcohol with a mean particle diameter of 90 μm to 500 μm, c) a disintegrating agent, and d) a cellulose compound.

2. The preparation according to claim 1, which contains 0.1 to 10 parts of the ingredient b-2) per 1 part of the ingredient b-1) by weight.

3. The preparation according to claim 1, wherein a mixture of the ingredient b-1) and the ingredient b-2) is used as the ingredient b-1) and the ingredient b-2).

4. The preparation according to claim 3, wherein the mean particle diameter of the mixture is 30 μm to 300 μm.

5. The preparation according to claim 1, wherein the mean particle diameter of the ingredient b-1) is 30 μm to below 90 μm.

6. The preparation according to claim 1, wherein the mean particle diameter of the ingredient b-1) is 35 μm to 80 μm.

7. The preparation according to claim 1, wherein the mean particle diameter of the ingredient b-2) is 90 μm to 300 μm.

8. The preparation according to claim 1, wherein the mean particle diameter of the ingredient b-2) is 90 μm to 200 μm.

9. The preparation according to claim 1, wherein the saccharide is one or more saccharides selected from the group consisting of glucose, fructose, lactose, sucrose, and trehalose.

10. The preparation according to claim 1, wherein the sugar is lactose.

11. The preparation according to claim 1, wherein the sugar alcohol is one or more sugar alcohols selected from the group consisting of D-mannitol, erythritol, xylitol, maltitol, and sorbitol.

12. The preparation according to claim 1, wherein the sugar alcohol is D-mannitol.

13. The preparation according to claim 1, wherein D-mannitol with a mean particle diameter of 30 μm to below 90 μm and D-mannitol with a mean particle diameter of 90 μm to 300 μm are used as the ingredient b-1) and the ingredient b-2), respectively.

14. A method for production of the preparation according to claim 1, which comprises compression molding a mixture containing a) an active ingredient, b-1) a saccharide or sugar alcohol with a mean particle diameter of 5 μm to below 90 μm, b-2) a saccharide or sugar alcohol with a mean particle diameter of 90 μm to 500 μm, c) a disintegrating agent, and d) a cellulose compound.

* * * * *